(12) United States Patent
Bordon et al.

(10) Patent No.: US 7,026,814 B2
(45) Date of Patent: Apr. 11, 2006

(54) TUNING OF NUCLEAR MAGNETIC RESONANCE LOGGING TOOLS

(75) Inventors: Ernesto Bordon, Houston, TX (US); Martin D. Hurlimann, Ridgefield, CT (US); Chanh Cao Minh, Katy, TX (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 10/742,481

(22) Filed: Dec. 19, 2003

(65) Prior Publication Data

US 2005/0156592 A1    Jul. 21, 2005

(51) Int. Cl.
   *G01V 3/00*        (2006.01)
(52) U.S. Cl. ..................................... 324/303
(58) Field of Classification Search ............... 324/303, 324/307, 309
   See application file for complete search history.

(56) References Cited

U.S. PATENT DOCUMENTS

| | | | | |
|---|---|---|---|---|
| 4,682,106 A | * | 7/1987 | Vatis et al. | 324/307 |
| 5,254,949 A | * | 10/1993 | McDonald et al. | 324/309 |
| 5,291,137 A | | 3/1994 | Freedman | 324/303 |
| 5,451,873 A | | 9/1995 | Freedman et al. | 324/303 |
| 6,046,588 A | * | 4/2000 | Watanabe | 324/307 |
| 6,064,206 A | * | 5/2000 | Van Vaals et al. | 324/312 |
| 6,111,408 A | * | 8/2000 | Blades et al. | 324/303 |
| 6,204,663 B1 | * | 3/2001 | Prammer | 324/303 |
| 6,470,274 B1 | * | 10/2002 | Mollison et al. | 702/7 |
| 6,472,872 B1 | * | 10/2002 | Jack et al. | 324/309 |
| 6,493,632 B1 | * | 12/2002 | Mollison et al. | 702/2 |
| 6,552,541 B1 | * | 4/2003 | Nauerth | 324/309 |
| 6,711,502 B1 | * | 3/2004 | Mollison et al. | 702/6 |
| 6,774,634 B1 | * | 8/2004 | Cosman | 324/321 |

OTHER PUBLICATIONS

Ernst, Richard R., Bodenhausen, Geoffrey and Wokaun, Alexander. *Principles of Nuclear Magnetic Resonance in One and Two Dimensions.* Oxford 1987. pp. 115-124.

* cited by examiner

*Primary Examiner*—Diego Gutierrez
*Assistant Examiner*—Dixomara Vargas
(74) *Attorney, Agent, or Firm*—Jody Lynn DeStefanis; William L. Wang; Dale Gaudier

(57) ABSTRACT

A method for tuning a nuclear magnetic resonance (NMR) tool having an operating frequency and equipped with an antenna, is disclosed comprising: (a) transmitting a rf magnetic field to a sample under investigation; (b) receiving an NMR signal from the sample within a detection window; (c) determining mistuning of said antenna relative to said operating frequency; (d) analyzing the received echo signal to determine mistuning of the received signal from the operating frequency. The mistuning of the received signals from the operating frequency may be determined by analyzing any changes in phase of the echo along the echo signal. The antenna tuning process may be automated by measuring calibrated signal amplitudes at more than one frequency and identifying a maximum amplitude. The system tuning may be maintained by repeating (a) through-(d) while operating the tool and implementing a feedback loop.

55 Claims, 13 Drawing Sheets

TUNING OF NUCLEAR MAGNETIC RESONANCE LOGGING TOOLS

BACKGROUND OF THE INVENTION

Pulsed nuclear magnetic resonance (NMR) measurements use bursts of electromagnetic fields (also called rf pulses) at a specific frequency (also called the operating frequency or rf frequency) to induce response echoes in the material under measurement. To obtain the maximum response to a particular element, the operating frequency should be at the "Larmor frequency" (also called the "sweet spot" of the instrument). The Larmor frequency is dependent upon local static magnetic fields, which may change during logging. For example, temperature changes or the accumulation of magnetic debris on the tool will affect the strength of the static magnetic field and influence logging measurements. Because the tool is calibrated relative to the Larmor frequency, changes in the static magnetic field must be accounted for, such as by changing the operating frequency of the pulses and the resonance frequency of the antenna.

Accordingly, two frequencies should be tuned for proper instrument operation: (1) the operating frequency should be set to the Larmor frequency taking into account local static fields and (2) the resonance frequency of the antenna should be set to the rf frequency.

Improper tuning of an NMR logging tool affects the porosity calibration in two distinct ways. First, the strength of the rf pulses in the formation is changed, which leads to a reduced precessing magnetization. Second, a given precessing magnetization will induce a smaller signal in the spectrometer.

The conventional method of tuning Schlumberger's CMR™ tool is described in commonly owned U.S. Pat. No. 5,451,873 to Freedman, et al. (the '873 Patent) (incorporated by reference herein in its entirety). In the method of the '873 Patent, the tool is positioned in front of a high porosity zone, preferably as a station stop and the rf (operating) frequency is estimated based on the temperature reading of the sonde. The antenna, which operates like a parallel-resonant LC circuit, is then tuned to this frequency by the so-called "tune word search task" (TWST). The TWST uses a continuous test signal at the operating frequency injected with constant current into the antenna. The tuning capacitor is then varied while monitoring the detected amplitude of a signal injected into a test loop located on the antenna. The value of capacitance that provides the largest amplitude is selected for the best tuning. The TWST has to be done before driving the antenna with the electromagnetic bursts.

With this antenna tuning, the rf frequency is then adjusted to the proper Larmor frequency at the sweet spot with the so-called "Larmor frequency search task" (LFST). According to LFST, the Larmor frequency is determined by taking a set of measurements of the relative echo signal amplitudes at different operating frequencies. This set of measurements is fitted to a predetermined response curve to obtain the frequency maximum amplitude. Essentially, the rf-frequency is varied to find the maximum NMR signal. This is time consuming and may require that the tool be stationary in the well.

The temperature of the magnet is then monitored during logging and the rf frequency is adjusted based on the known temperature coefficient of the magnet material. A Hall probe may also be used to measure the magnetic field strength inside the sonde and detect accumulation of magnetic debris on the magnets.

The LFST cannot be performed during a NMR measurement and, therefore, needs to be performed beforehand. Accordingly, all other factors that affect amplitude need to remain constant during the LFST.

The LFST is a slow procedure because, for every setting of rf frequency, the amplitude has to be measured with a good signal to noise ratio. This is not always practical. A formation of at least 10 pu is required to accomplish the tuning procedure in which the signal strength for seven (7) different rf frequencies is measured and the optimal rf frequency and corresponding antenna tuning is inferred. During this time, the porosity in front of the tool must be constant, requiring a station stop in most cases. However, in many logging environments, station stops are not possible. Further, in fluid sampling tools, the flowing fluid will not likely have a constant hydrogen index.

During a continuous log it is not possible to verify directly that the operating frequency is tracking any changes in the Larmor frequency. Predictable changes occur due to changes in the temperature of the magnets that create the static field. The change of the magnet's field with temperature is a known magnitude and so the operating frequency can be corrected approximately by a measure of the sonde temperature. However, a sudden change in the magnetic field caused by magnetic particles attracted and deposited on the magnets can cause unknown shifts in the Larmor frequency that invalidate the tool calibration. To attempt detection of such shifts the magnetic field is measured in the vicinity of the zone under measurement. But this determination is coarse and does not allow for quantitative correction of the shifts.

Accordingly, there is a need for a continuous measurement of any deviation of the operating frequency from the Larmor frequency during the NMR measurement to allow the operating frequency to track this deviation by means of a feedback loop and so maintain the instrument calibrated throughout the measurement.

There is presented herein an improved method to continuously tune NMR logging tools, which accounts for changes in static magnetic fields.

SUMMARY OF THE INVENTION

In accordance with the present invention, the echo signal is analyzed to detect any mistuning of the rf frequency from the Larmor frequency. Likewise, either an independent measurement or the echo signal phase is used to monitor the detuning of the rf frequency with respect to the resonance frequency of the antenna. For the purposes of the present invention, the term "antenna" is the system component that transmits the rf magnetic field and detects the magnetic field due to the NMR precession, such as an NMR coil. The tuning of the antenna and the tuning of the rf frequency with respect to the Larmor frequency may be adjusted, if necessary. This "retuning" can be done continuously while logging to account for any local changes in the static magnetic field, allowing proper tuning of the tool to be maintained while logging and reducing the need for conventional off-line time-consuming tuning procedures. The resulting improvements are a reduction of systematic errors in porosity determination and the optimization of the signal to noise ratio.

The tuning procedure of the present invention is based on information obtained from the NMR signal and may be implemented using the presently used pulse sequences, in particular sequences based on the CPMG sequence. Therefore, the tuning is measured as seen by the spins without requiring a change in the pulse sequence or the introduction of additional signals into the antenna.

Before this method is implemented for a given NMR logging tool, its electronics should preferably be calibrated and characterized during a master calibration phase. For example, temperature dependence of the electronics, such as phase shifts versus temperature, should be identified.

It is noted that the method of the present invention is best used to maintain the tuning of the tool. However, the method may be used to initially calibrate the system. If the method is used to initially calibrate the system, the higher order terms in Equation (5) (discussed below) may be significant. In this case, it may be necessary to iterate the tuning procedure. Alternatively, it might be more efficient to use the conventional procedure to determine the approximate tuning and then implement the method of the present invention to refine and maintain the tuning of the tool.

The present method to measure detuning of the rf frequency from the Larmor frequency by analyzing the echo signal is based on changes in the phase of the echo signal with respect to the rf phase along the echo interval. In a preferred embodiment, the signal is amplified, converted to an intermediate frequency, detected by a phase-sensitive demodulator and integrated over the duration of the echo. A measurement of the signal phase relative to a reference (the instrument's rf frequency) is implicit in the signal demodulation. Therefore, in addition to integrating the whole echo, the interval of duration of the echo is partitioned into several zones (or intervals), the simplest case being the two halves of the echo. Each of the zones is integrated independently, obtaining for each zone the amplitude and a phase value relative to the operating frequency source. Although any measurements of absolute phase are not stable and, therefore, are of little use, the relative phase differences between the integrated zones change with the difference between operating frequency and Larmor frequency. So the deviation from the Larmor frequency correlates nearly linearly with the phase differences measured between zones along the echo.

These phase differences measured are affected in large extent by the antenna detuning (deviation of the resonance frequency of the antenna from the operating frequency). Therefore, the present invention includes means to continuously measure antenna detuning and correct the phase differences for this effect.

Accordingly, in one embodiment of the present invention (as shown in FIG. 17), a method for tuning a nuclear magnetic resonance (NMR) tool having an operating frequency and equipped with an antenna, is disclosed comprising: (a) transmitting a rf magnetic field to a sample under investigation 100; (b) receiving an NMR signal from the sample within a detection window 200; (c) determining mistuning of the antenna relative to the operating frequency 300; (d) analyzing the received echo signal to determine mistuning of the received signal from the operating frequency 400. Alternatively, the complex echo shape of the received echo signal may be analyzed. For the purposes of this patent application, "complex echo shape" includes components from both the in-phase and out-of-phase channels. In a second embodiment, the mistuning of the received signals from the operating frequency is determined by analyzing any changes in phase of the echo along the echo signal. Accordingly, signal shape may be quantified by analyzing changes in phase along the echo signal.

The antenna tuning process may be automated by measuring the amplitudes of calibration signals generated at more than one frequency. These amplitudes may be analyzed to determine mistuning of the antenna relative to the operating frequency. In one embodiment, a maximum amplitude may be identified to determine antenna mistuning. The system tuning may be maintained by repeating (a) through (d) while operating the tool and implementing a feedback loop. Further, the effects of the antenna mistuning may be minimized by performing (c) and (d) nearly simultaneously.

The detection window may be partitioned into more than one interval and in-phase and out-of-phase signals detected in each interval. These signals may be analyzed to determine mistuning of the received echo signal from the operating frequency. Any combination of in-phase signals and out-of-phase signals may be analyzed. For example, two in-phase signals from different intervals may be analyzed or two out-of-phase signals from different intervals may be analyzed. Alternatively, in-phase and out-of-phase signals from the same or different intervals may be analyzed. The slope of a signal detected in the out-of-phase channel may be determined at the signal (echo) center. The tuning of the operating frequency may be inferred from the out-of-phase slope. The out-of-phase slope may be approximated by determining the ratio of the out-of-phase portion of the detection window versus the in-phase portion of the detection window according to the ratio $\mathcal{R}$ defined below. The measurement of $\mathcal{R}$ may be refined by taking multiple measurements to determine ratio $\mathcal{R}$ for more than one echo and calculating an average $\mathcal{R}$.

Mistuning of the antenna may be determined by comparing the signal phase of the received signal to the signal phase of the transmitted signal. In particular, the tuning of the antenna may be inferred based on the difference in phase between the received signal and the transmitted signal such as by: (a) transmitting an rf magnetic field at the operating frequency modulated by an amount approximately equivalent to the width of the antenna resonance; (b) receiving an NMR signal; and (c) comparing the received signal to the operating frequency of the modulated magnetic field. Further, the intensity of sidebands corresponding to the modulated rf magnetic field and the received signal may be measured to assist in this analysis.

Further features and applications of the present invention will become more readily apparent from the figures and detailed description that follows.

DETAILED DESCRIPTION

Figure 1:
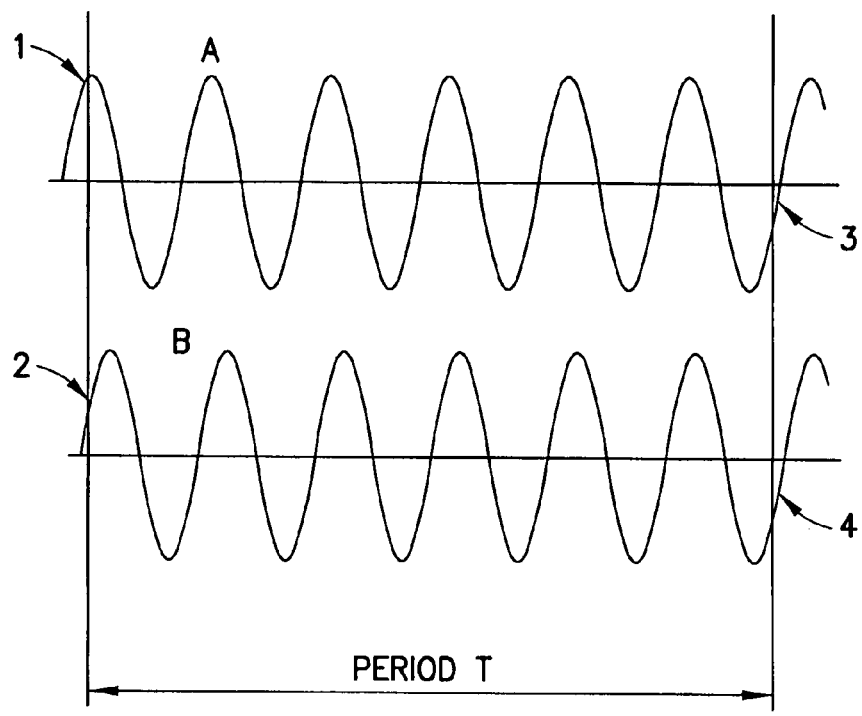
FIG. 1 is a schematic showing two phase measurements that allows measurement of detuning of the operating frequency.

In an embodiment of the present invention, mistuning of the rf frequency from the Larmor frequency is measured wherein the main frequency component of the echo signal (Larmor Frequency) is compared with the rf frequency (frequency of the rf signals transmitted by the instrument and the reference of the phase-sensitive echo demodulation) by two or more phase measurements of the echo signal at fixed time intervals along the echo. This principle is illustrated in FIG. 1, which shows two phase measurements, phase1 and phase2, separated by a period T, resulting in the measurement of detuning as proportional to (phase2−phase1)/T. More particularly, FIG. 1 shows an echo signal (A) and a detector reference (calibration signal) at rf frequency (B). Measured phase1 is the difference between phases of the echo signal at 1 [ph1(1f)] and the detector reference at 2 [ph1(r)]. Accordingly, phase1=ph1(1f)−ph1(r). Measured phase2 is the difference between phases of echo signal at 3 [ph1(1f)+wlf*T] and detector reference at 4 [ph1(r)+wrf*T], where wlf is 2π(1f) and wrf is 2π(rf). Accordingly, measured phase2=[ph1(1f)+wlf*T]−[ph1(r)+wrf*T]=phase1+(wlf−wrf)*T. Detuning of the operating frequency (wo) is the difference between wlf and wrf and may be written as (phase2−phase1)/T.

In practice, to measure the amplitude of the echoes (the primary data acquired by this instrument) the signal from the antenna is amplified, converted to an intermediate frequency, filtered and digitized by a fast analog to digital converter (ADC) during the time of the echo. Once digitized, the data is processed by a fast digital signal processor (DSP) that performs phase-sensitive demodulation and digital integration, resulting in a set of values for each echo that reflect its amplitude and phase. By partitioning the measurement time of the echo and performing the above described processing to a certain number of sub-periods, it is possible to determine the change in instantaneous phase of the signal along the echo. In the simplest case, the echo signal is digitally integrated over its two halves, and demodulated into the orthogonal R and X signals for each. From these the values of sine and cosine of the phase angle for each half are computed and the phase difference is extracted from these as described above and illustrated below.

Figure 2:
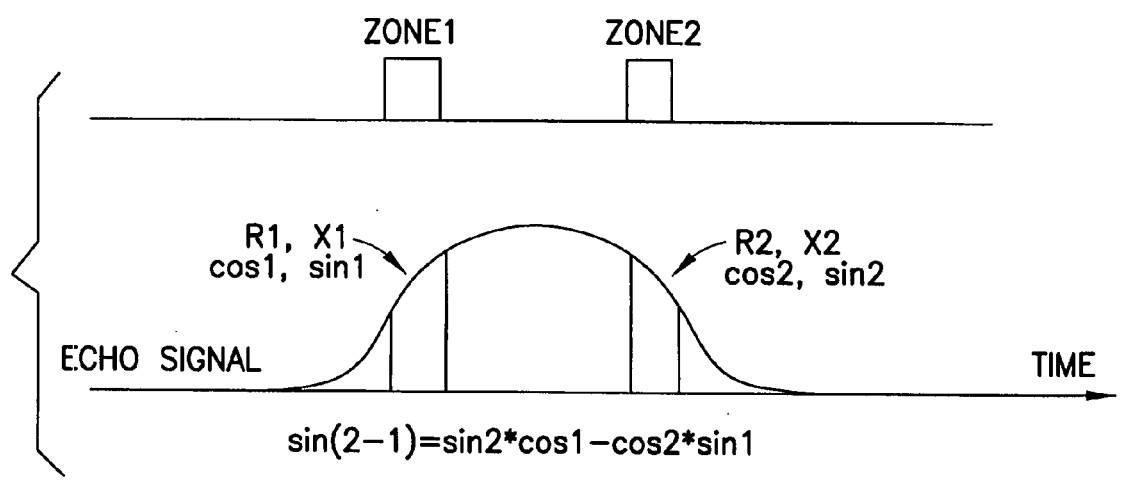
FIG. 2 is a schematic showing the measurement of phase difference for multiple zones as modeled using two zones.

It was verified that the increase in phase along the echo (phase of the later part minus phase of the earlier part) increases in proportion to the difference between the operating frequency and the Larmor frequency. The calculation shown in FIG. 2 is a simple approximate way to measure this phase increase (phase difference).

The phase values from multiple zones along the echo may be calculated in various ways. For practical purposes, a flexible implementation can be limited to two zones as shown in FIG. 2, of selectable sizes and positions along the echo, and the phase difference between the two may be analyzed. One skilled in the art would recognize that the sizes and positions in the echo of the two zones can be selected for optimum signal-to-noise ratio. Additional zones may also be used.

Figure 3:
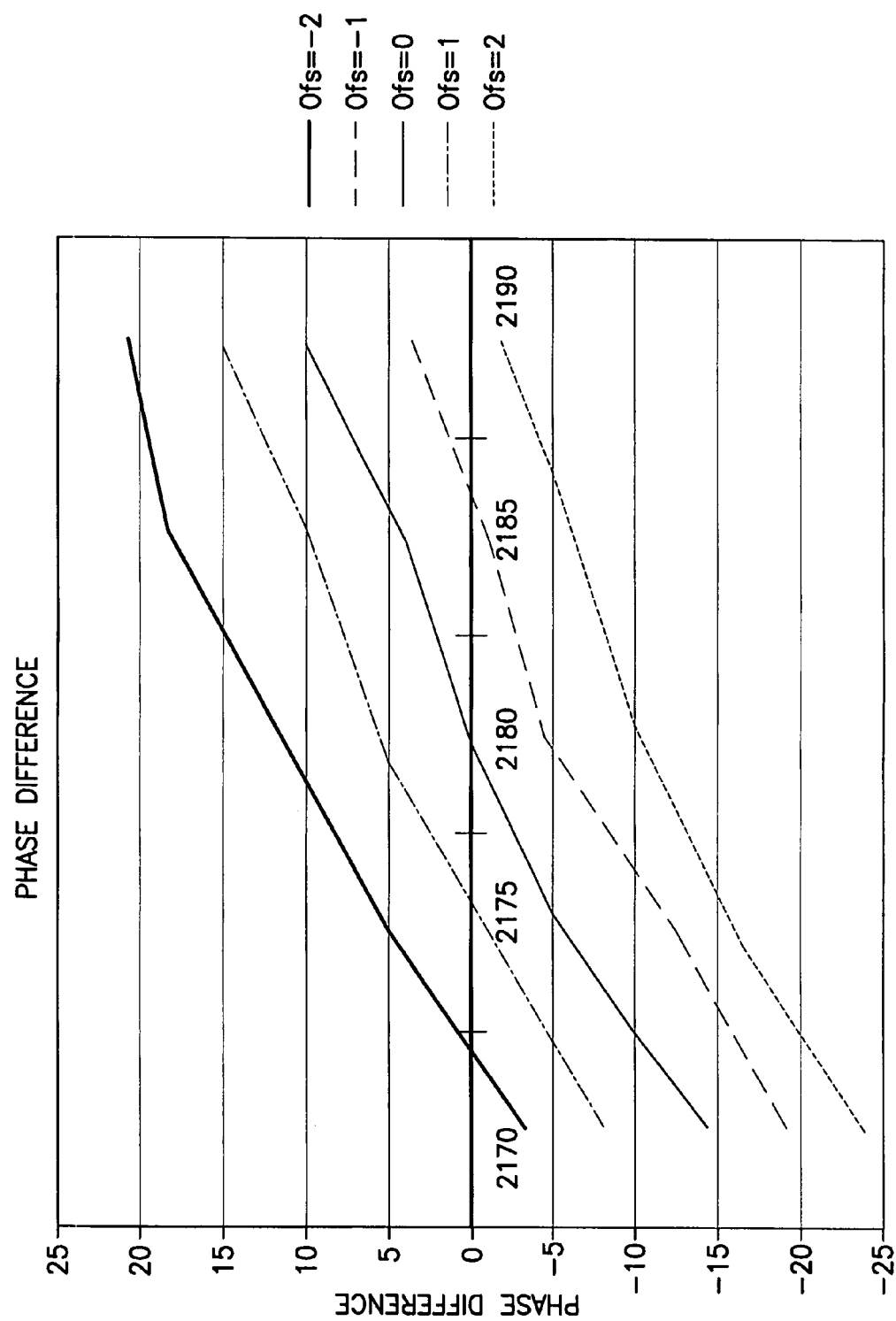
FIG. 3 is a graph showing the phase difference in degrees as a function of operating frequency for a set of measurements for different values of antenna-tuning offsets.
Figure 4:
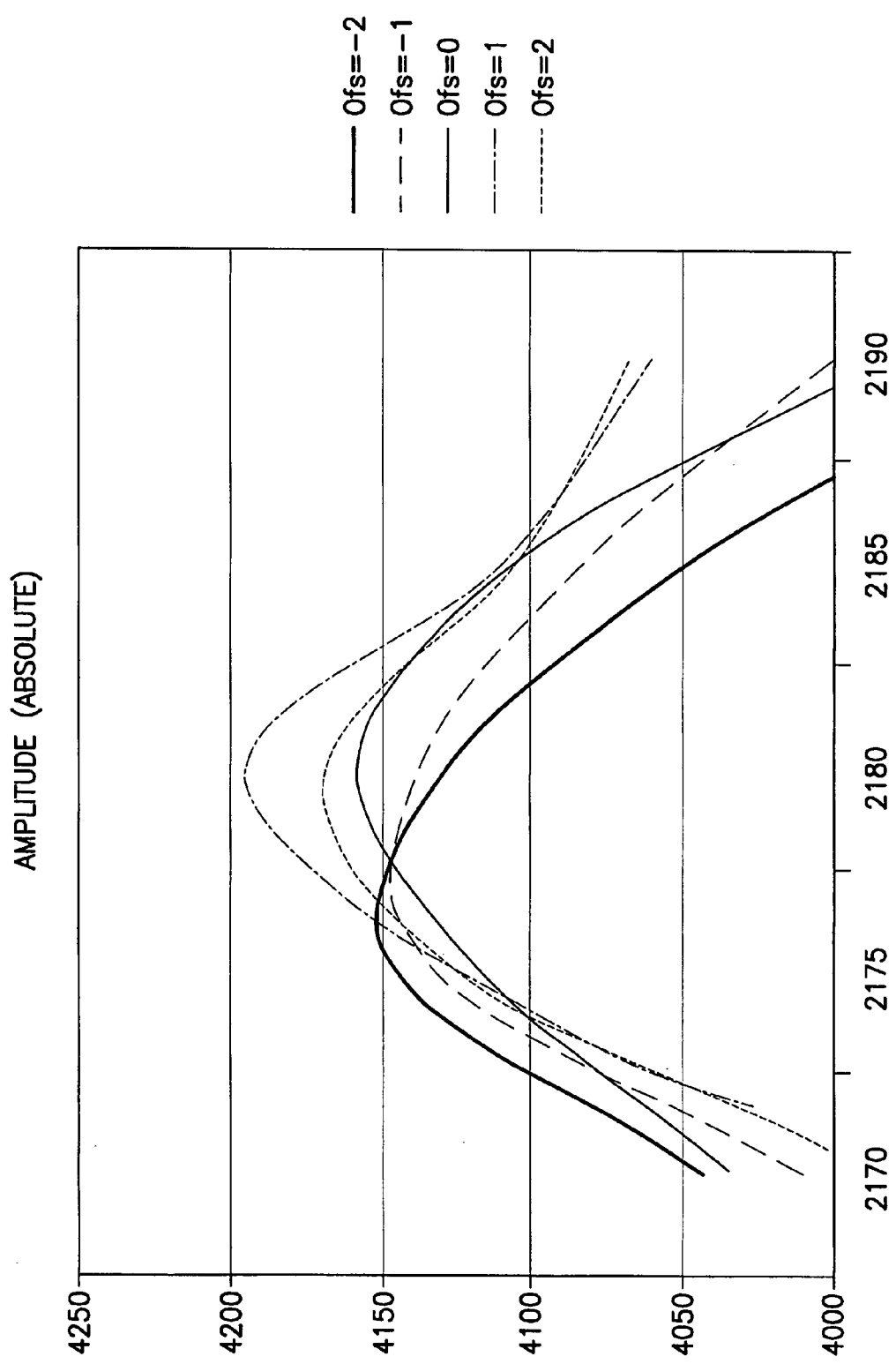
FIG. 4 is a graph showing signal amplitude as a function of operating frequency for the same set of measurements of FIG. 3.

By way of example, the present invention was implemented using Schlumberger's CMRT-A version of the CMR™ tool. Results of phase difference measurements taken with Schlumberger's CMRT-A tool using the standard water bottle as the measurement sample are shown in FIGS. 3 and 4. The Larmor frequency of the tool in this setup is 2180 kHz. The phase differences are taken between two zones that are the two halves of the echo. Each figure shows a set of curves, with parameter that is the tune-word offset between −2 and 2 (at approximately 1 kHz per tune-word), each taken with measure points every 5 kHz. The set of curves shows the dependence of the response on the antenna tuning.

FIG. 3 shows the phase difference in degrees as function of operating frequency, measured at intervals of 5 kHz. The center curve, corresponding to a zero tune-word offset, crosses zero at the Larmor frequency, 2180 kHz. The curves show a close to linear response with frequency deviation.

FIG. 4 depicts signal amplitude as a function of operating frequency. For the curve corresponding to zero tune-word offset, the maximum amplitude occurs at 2180 kHz, therefore the Larmor frequency.

The set of curves in FIGS. 3 and 4 show, as expected, that antenna detuning largely affects the phase difference values. When the antenna is tuned by discrete capacitance changes it is not possible to reach exact tuning at a given frequency and the quantitative measurement of antenna detuning provides a means to correct for small detuning values. With a combination of capacitance and frequency changes for antenna tuning, the detuning can be reduced to a level that does not significantly affect the phase differences.

Figure 5:
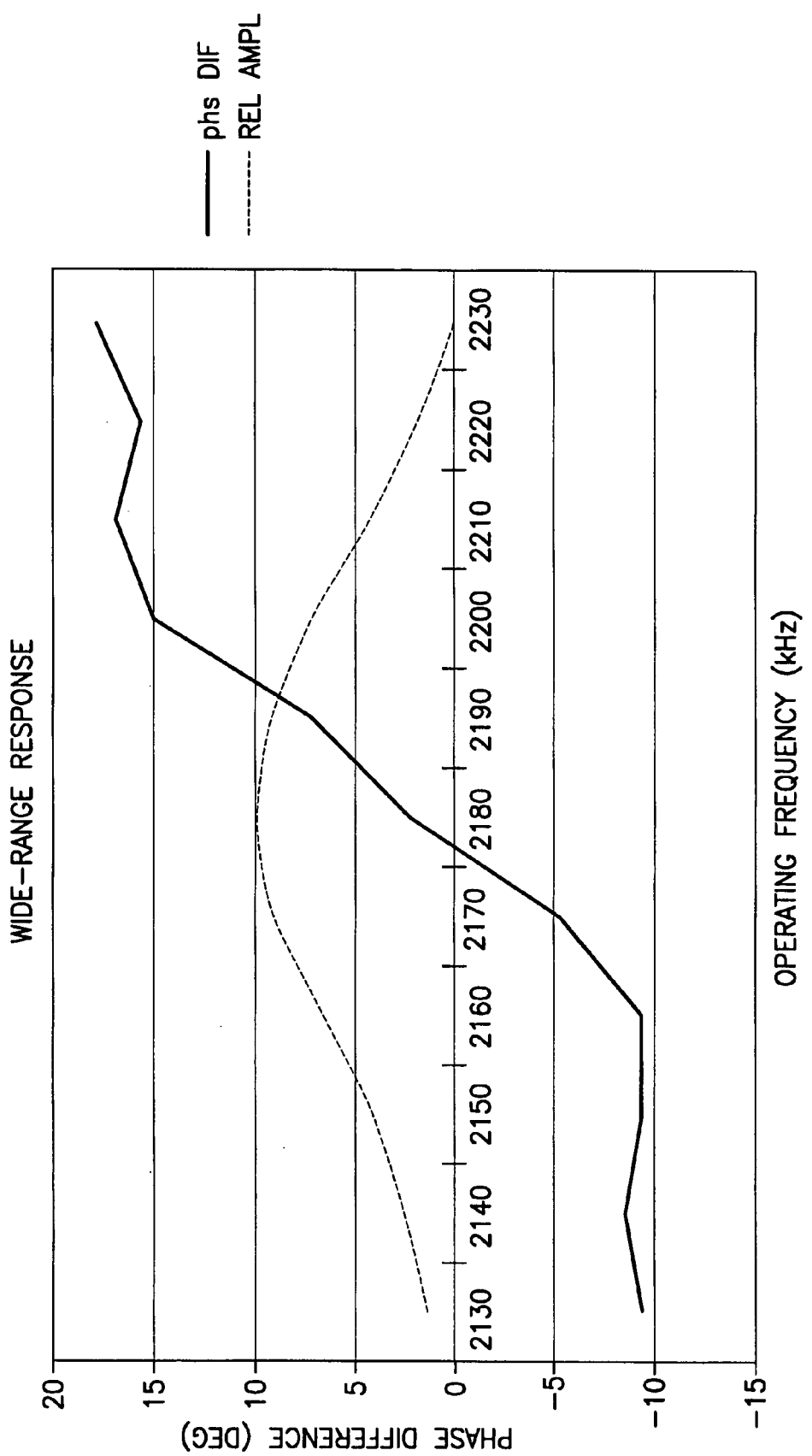
FIG. 5 is a graph showing phase difference over a wide operating frequency range.

FIG. 5 shows the behavior of the phase difference over a frequency interval of 100 kHz, showing the wide range of this measurement. In this example with an interval of 100 kHz (about one third of the CMR™ tool frequency range), the phase-difference curve shows good potential for a feedback loop to capture the Larmor frequency point. The relative amplitude curve is expanded and offset to show clearly the maximum (Larmor frequency.)

Another method of the present invention takes advantage of the information that is contained in the overall phase of the signal and in its out-of-phase (or "noise") channel. The analysis presented below shows that the signal in this channel is antisymmetric with time relative to the echo center. It is shown here that the amplitude of the antisymmetric signal is related to the detuning of the rf frequency with respect to the Larmor frequency ad to the detuning of the antenna resonance frequency with respect to the rf frequency.

Echo Amplitude

The signal generated from any position in space depends on the timing of the pulse sequence and the following two frequencies: $\omega_0 \equiv \gamma|\vec{B}_0|-\omega_{rf}$, and $$\omega_1 \equiv \frac{1}{2}\gamma|\vec{B}_{1\perp}|.$$

Here $\vec{B}_{1\perp}$ is the component of $\vec{B}_1$ that is orthogonal to $\vec{B}_0$, $\omega_0$ measures the detuning of the static field from resonance, and $\omega_1$ is proportional to the rf field strength.

The asymptotic expression for the transverse magnetization in the rotating at the time of the formation of the echo for the standard CPMG sequence is given by:

$$\vec{M}_\perp(\omega_0, \omega_1) = M_0 \frac{\omega_1}{\Omega} \frac{\sin(\Omega t_{\pi/2})}{1 + \left[\frac{\Omega}{\omega_1}\sin(\omega_0 t_E/2)\cot(\Omega t_\pi/2) + \frac{\omega_0}{\omega_1}\cos(\omega_0 t_E/2)\right]^2} \hat{y} \quad (1)$$

where $M_0$ is the thermal equilibrium magnetization, $\Omega = \sqrt{\omega_0^2+\omega_1^2}$, $t_{\pi/2}$, $t_\pi$ are the duration of the $\pi/2$ and $\pi$ pulses, respectively, and $t_E$ is the echo spacing. This is the asymptotic form for large number of echoes, but it has been shown that in inhomogeneous fields it is approached by the third echo. Note in particular that for all values of $(\omega_0,\omega_1)$, $\vec{M}_\perp$ has only a component along the $\hat{y}$ axis. The asymptotic echoes of a CPMG pulse sequence in grossly inhomogeneous fields therefore have a pure absorption spectrum.

The detected signal, centered at an echo time $t_0$, is proportional to:

$$S_0(t_0+t) = \int\int d\omega_0 d\omega_1 (\omega_{rf}+\omega_0)\omega_1 F(\omega_0,\omega_1) M_\perp(\omega_0,\omega_1) e^{j\omega_0 t} \quad (2)$$

Here $F(\omega_0,\omega_1)$ is the distribution function of $\omega_0$ and $\omega_1$ for the particular tool, defined such that $F(\omega_0,\omega_1)\Delta\omega_0\Delta\omega_1$ is proportional to the number of spins that are exposed to a static field in the range of $\omega_0\pm\Delta\omega_0/2$ and an rf field in the range of $\omega_1\pm\Delta\omega_1/2$. The factor $(\omega_{rf}+\omega_0)\approx\omega_{rf}$ is due to Faraday detection. The factor $\omega_1$ accounts for the antenna efficiency.

Field Profiles

Equation (2) is written in the rotating frame that rotates with the rf frequency of the pulses. This corresponds directly to the demodulated signal that is being observed in the spectrometer. The signal is affected when the rf frequency is changed by $\Delta\omega_{rf}$.

The excitation spectrum $M_\perp(\omega_0,\omega_1)$ is centered at the rf frequency of the pulses and is therefore independent of the rf frequency (except weakly through $M_0$). In contrast, the distribution function $F(\omega_0,\omega_1)$ depends on the static field profile. In the rotating frame, $F(\omega_0,\omega_1)$ changes with the offset between the rf frequency and the Larmor frequency in a zone wherein the static magnetic field is influenced (also known as "a sensitive zone"). When the rf frequency is changed by $\Delta\omega_{rf}$ the distribution function should be translated to a new rotating frame, resulting in $F(\omega_0,\omega_1) \rightarrow F(\omega_0-\Delta\omega_{rf},\omega_1)$.

There are two extreme cases. In a typical laboratory set-up both the static and rf fields are very homogeneous. In this case, the distribution function is essentially a delta function: $F(\omega_0,\omega_1)\approx\delta(\omega_0-\omega_{0,lab})\delta(\omega_1-\omega_{1,lab})$. All the spins have the same Larmor frequency. If the rf frequency deviates strongly from this Larmor frequency, all the spins will be excited off-resonance and there will be a large decrease in the detected signal. On the other extreme, if the applied fields have a constant gradient, the distribution function is flat and independent of offset frequency $\omega_0$: $F(\omega_0,\omega_1)\equiv$constant. For any value of rf frequency, they are always roughly the same number of spins on resonance. Changing the rf frequency does not change the detected signals, it only changes the physical place where the signal is generated from.

Figure 6A:
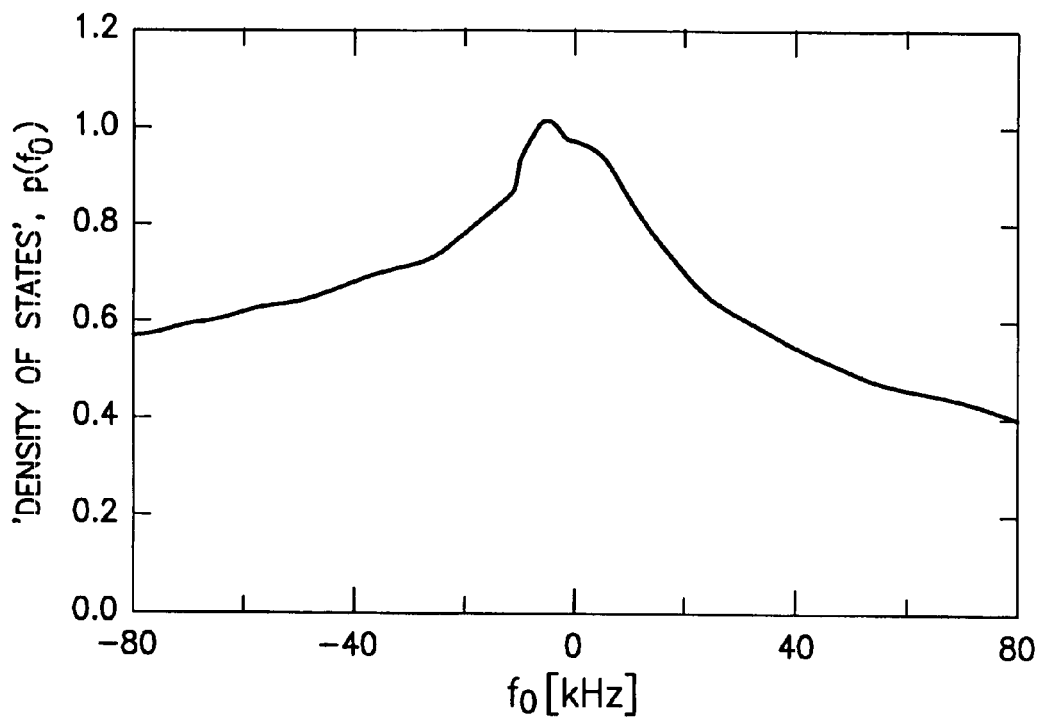
FIGS. 6(a) and (b) are graphs showing "density of states" for logging and fluid sampling tools.
Figure 6B:
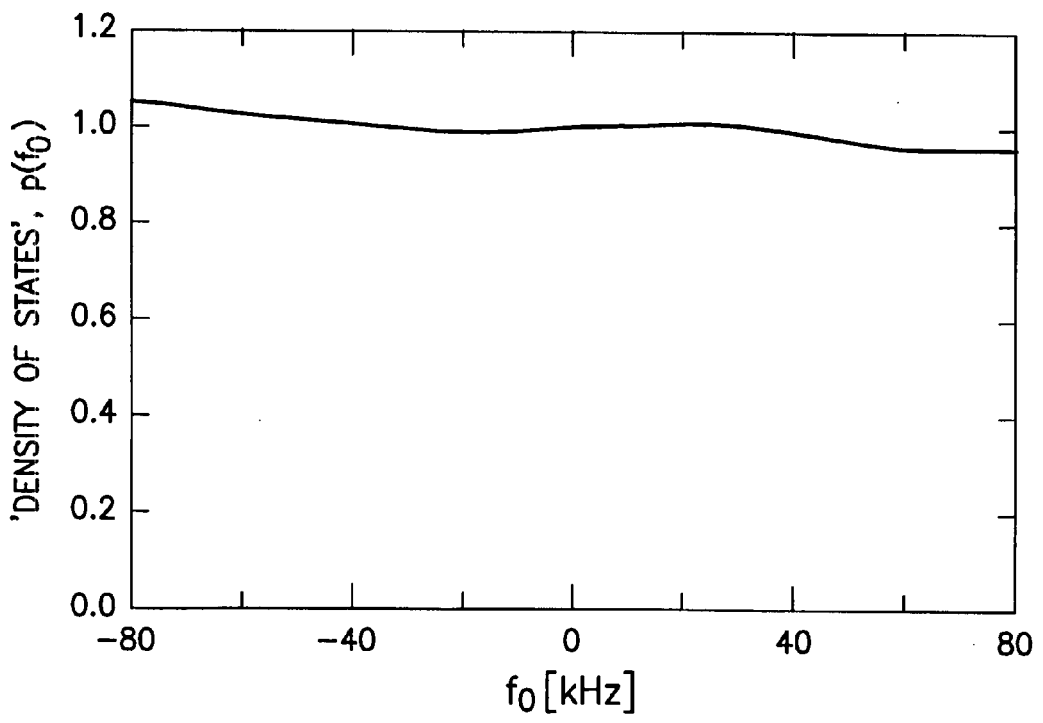

Some tools, such as Schlumberger's CMR™ tool, are designed somewhere between these two extremes. The field is very inhomogeneous, but there is a saddle point where the fields are more homogeneous. By contrast, some tools, such as Schlumberger's MRX™ and MDT™ tools, are closer to the second extreme. This is illustrated in FIGS. 6(a) and (b) which are plots of the integral of the net distribution function $\omega_1 F(\omega_0,\omega_1)$ over the rf field strength $\omega_1$: $\rho(f_0) = \int d\omega_1 F(\omega_0,\omega_1)\omega_1$. [These plots include the effect of the antenna efficiency.] The functions were calculated based on the measured field maps. The function $\rho(f_0)$ can be treated as a density of states. These plots show the projections of $\rho(f_0) = \int d\omega_1 F(\omega_0,\omega_1)\omega_1$ of the distribution function $\omega_1 F(\omega_0,\omega_1)$ as a function of the Larmor frequency offset $$f_0 = \frac{\omega_0}{2\pi},$$

normalized to 1 at $f_0$ equal to 0. For tools with a saddle point (FIG. 6(a)), $\rho(f_0)$ is peaked at a frequency corresponding to the Larmor frequency of the saddle point. In contrast, for tools without a saddle point, the density of states is nearly horizontal, as shown in FIG. 6(b).

Echo Shape: rf/Larmor Frequency Tuning

To the first order, the signal of the spin echo in the rotating frame can be written as:

$$S(t) = e^{-j\frac{4Q_l}{\omega_c}(\omega_{rf}-\omega_c)} \int d\omega_0 f(\omega_0)\exp\left\{j\omega_0\left(t - \frac{2Q_l}{\omega_c}\right)\right\} \quad (3)$$

Here $\omega_c$ is the resonance frequency of the coil, $\omega_{rf}$ is the rf frequency of the NMR pulses, and $Q_l$ is the loaded quality factor of the coil. $f(\omega_0)$ is the spectrum of the signal. The frequency $\omega_0$ is the difference between the local Larmor frequency and the rf frequency. The time t is measured with respect to the center between two adjacent $\pi$ pulses. The spectrum $f(\omega_0)$ depends on the details of the pulse sequence and the field maps of the logging tool. For the standard CPMG sequence, the analysis shows that the spectrum $f(\omega_0)$ is purely real after the first few echoes.

The first order result of Equation (3) shows several important features. The finite bandwidth of the antenna delays the echo by a time $$\frac{2Q_l}{\omega_c}.$$

This delay is in addition to any other delays that might be intrinsic to the electronics of the tool. With respect to the new echo center, the signal in the in-phase channel is symmetric and in the out-of-phase channel is antisymmetric with time. Further, the overall phase of the signal is only related to the detuning of the coil from the rf frequency, $\omega_{rf}-\omega_c$. The measured phase can therefore be used to infer the tuning of the antenna.

The slope of the out-of-phase signal at the echo center is directly related to the first moment of the spectrum $\bar{\omega}_0$, which is a sensitive indicator of the tuning of the rf frequency with respect to the Larmor frequency at the sweet spot of the magnet. As will be discussed below, a ratio $\mathcal{R}$ that approximates the slope of the out-of-phase signal can be measured more robustly from the signal. $\mathcal{R}$ is independent of porosity and can be used to indicate the tuning of the rf frequency of the NMR pulses with respect to the Larmor frequency at the sensitive zone of the formation.

Figure 7:
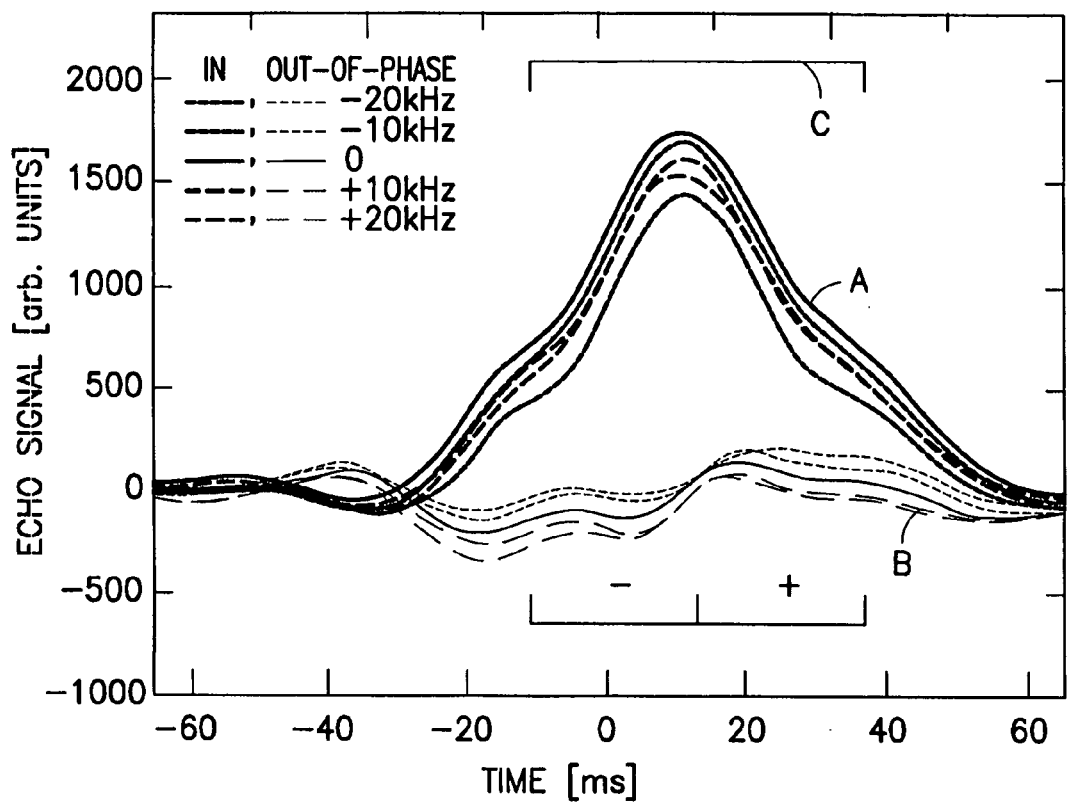
FIG. 7 is a graph of the in-phase and out-of-phase echo shapes for different applied fields between −20 kHz and +20 kHz, where the rf frequency is fixed at 1763 kHz.

The detuning of the rf frequency of the NMR pulses from the Larmor frequency at the sweet spot can be inferred from the shape of the spin echoes. It is important to use the information from both the in-phase and the out-of-phase channel (i.e. the signal in the two channels after the phasing procedure has been performed). FIG. 7 shows the echo shapes in the two channels for different applied fields. When the applied field is non-zero, the Larmor frequency at the sweet spot deviates from the rf frequency. As this happens, the amplitude of the in-phase echo decreases, without substantially changing the shape of the signal in this channel. If this is the only information that is collected, it could be misinterpreted as a decrease in porosity. However, detuning and porosity decrease may be distinguished by taking advantage of the extra information in the out-of-phase channel. When the Larmor frequency at the sweet spot changes, the out-of-phase signal changes significantly. The shape and the relative amplitude to the in-phase signal can be used to estimate the deviation of the rf frequency from the Larmor frequency at the sweet spot, including the sign of the deviation.

As mentioned above, it is useful to introduce the following ratio $\mathcal{R}$:

$$\mathcal{R} \equiv \frac{\left\{\int_{t_0}^{t_0+\frac{T}{2}} - \int_{t_0-\frac{T}{2}}^{t_0}\right\} dt\, S_{out-of-phase}(t)}{\int_{t_0-\frac{T}{2}}^{t_0+\frac{T}{2}} dt\, S_{in-phase}(t)} \quad (4)$$

where $S_{in-phase}$ and $S_{out-of-phase}$ are the in- and out-of-phase echo shapes, respectively, $t_0$ is the center of the echo, and T is the total duration of the two detection windows.

The ratio of the out-of-phase signal ($S_{out-of-phase}$) to the in-phase signal ($S_{in-phase}$) can be expressed in terms of an instantaneous signal phase $$\psi(t): \frac{S_{out-of-phase}(t)}{S_{in-phase}(t)} = \tan\psi(t).$$

The ratio $\mathcal{R}$ can therefore be rewritten as a phase difference, $\mathcal{R} = \tan\psi_1 - \tan\psi_2 \approx \psi_1 - \psi_2$ where $\psi_1, \psi_2$ are the signal phases averaged over the in-phase and out-of-phase channels (detection windows).

Figure 8:
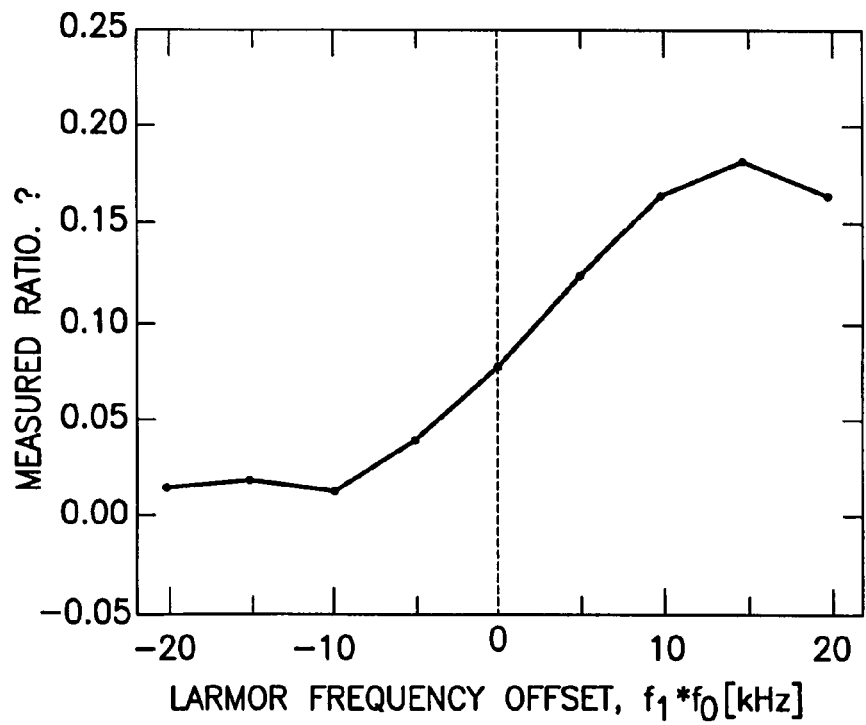
FIG. 8 is a graph showing measured ratio ℛ versus Larmor frequency offset.

$\mathcal{R}$ is independent of porosity is related to the peak frequency of the spectrum of the measured signal and therefore indicates the tuning of the rf frequency with respect to the Larmor frequency in the formation. In the current data collection and analysis of a tool with a saddle point, the echo signal is integrated over a window of duration T, centered at the echo, in both the in-phase (A) and out-of-phase (B) channels as shown in FIG. 7. The detection window is indicated as bracket C at the top of FIG. 7. In order to calculate $\mathcal{R}$ from the signal, the current window is split into two separate intervals or zones, shown in the bottom of FIG. 7. [It is noted that any number of intervals may be used.] This implies that twice as much data has to be acquired, but without increasing the number of rf pulses applied. FIG. 8 shows measurements of $\mathcal{R}$ versus the applied field for data collected using an NMR tool, setting the rf frequency at 1763 kHz.

The expected shapes of the acquired echoes do not change significantly after the second echo of a CPMG sequence. Therefore, many echoes may be averaged to get a better determination of $\mathcal{R}$, similar to the procedure commonly performed to determine phase. In addition, the tuning is not expected to change rapidly during logging. This allows the stacking of echoes of many adjacent CPMG sequences, this further decreasing the uncertainty in the determination of $\mathcal{R}$.

The ratio $\mathcal{R}$ defined in Equation (4) is just one particularly simple way to obtain a tuning parameter. The location and duration of the integration intervals has to be optimized for the best performance for a given logging tool.

One generalization of the tuning indicator $\mathcal{R}$ defined above in Equation (4) is to modify the flat top integrations in Equation (4) with windowing functions. There will be a trade-off in better noise performance versus complexity in signal acquisition and processing.

For the NMR tool used, the Larmor frequency offset is preferably less than ±7.5 kHz for an error of less than 3% in porosity. This corresponds to a 1 pu error in a 30 pu formation. In this range, FIG. 8 shows that the dependence of $\mathcal{R}$ on Larmor frequency offset is linear. A deviation of the measured value of $\mathcal{R}$ from the nominal value at resonance, $\mathcal{R}_0$, is directly related to the rf frequency offset from the Larmor frequency at the sweet spot. Resonance here is defined as the frequency for which the integrated in-phase signal shows a maximum.

The exact value of $\mathcal{R}_0$ is not necessarily zero, but will depend on the $(\vec{B}_0, \vec{B}_1)$ field maps in the sensitive zone of the specific logging tool. For the NMR tool used, $\mathcal{R}_0$ is determined to be equal to 0.08.

When the antenna resonance frequency is off-resonance, the spectrum of the detected signal will be somewhat distorted. This will affect the measured value of $\mathcal{R}$. Close to resonance $\mathcal{R}$ can be expanded linearly around $\mathcal{R}_0$:

$$\mathcal{R} \approx \mathcal{R}_0 + \alpha(f_L - f_{rf}) + \beta(f_c - f_{rf}) \quad (5)$$

This second term does not cause any significant problems. Once $\beta$ has been determined for a given logging tool, the second term can be subtracted, because the detuning $(f_c - f_{rf})$ can be determined independently from the measurement of the overall phase, as discussed below. In this way, the detuning $(f_L - f_{rf})$ can be extracted from the measured value of $\mathcal{R}$.

Signal Phase: Antenna Tuning

In NMR logging tools, the data is acquired in two channels. It is a standard procedure to rotate the data by an angle φ so that the integrated echoes show a coherent signal in one channel and noise in the other. (A description of this procedure applied to Schlumberger's CMR™ tool can be found in commonly owned U.S. Pat. No. 5,291,137 to Freedman, incorporated by reference herein in its entirety.)

The analysis of the spin dynamics in inhomogeneous fields coupled to a tuned circuit as mentioned above shows that the phase φ of the signal depends predominantly on the detuning of the resonance frequency of the antenna (or coil),$f_c$, from the rf frequency $f_{rf}$:

$$\tan(\varphi) = -2Q_l\left(\frac{f_{rf}}{f_c} - \frac{f_c}{f_{rf}}\right).$$

Here $Q_l$ is the loaded quality factor of the antenna. Note that to the first order, there is no dependence on the Larmor frequency at the sweet spot. Close to resonance, the phase change can be approximated by:

$$\Delta\varphi \cong -\frac{4Q_l}{f_c}(f_{rf} - f_c) \quad (6)$$

Figure 9:
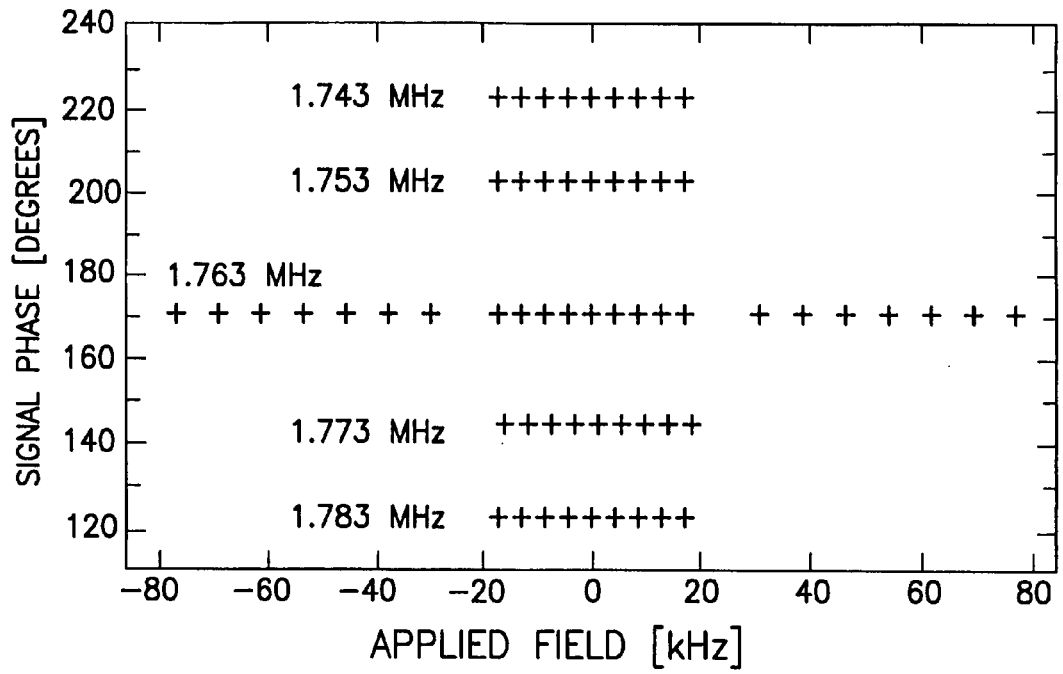
FIG. 9 is a graph showing the measured phase of NMR signal versus applied field for five different rf frequencies.

FIG. 9 shows supporting results of measurements of a magnetic resonance tool. In these measurements, the rf frequency was set at one of the five values indicated. An external field could be applied that varied the Larmor frequency at the sweet spot by an amount of between about −80 kHz and +80 kHz. The measured phases of the echoes of the CPMG sequence show a strong dependence on rf frequency, but they are essentially independent of the Larmor frequency at the sweet spot. As shown in the graph, the phase depends strongly on the rf frequency and weakly on the applied field.

Figure 10:
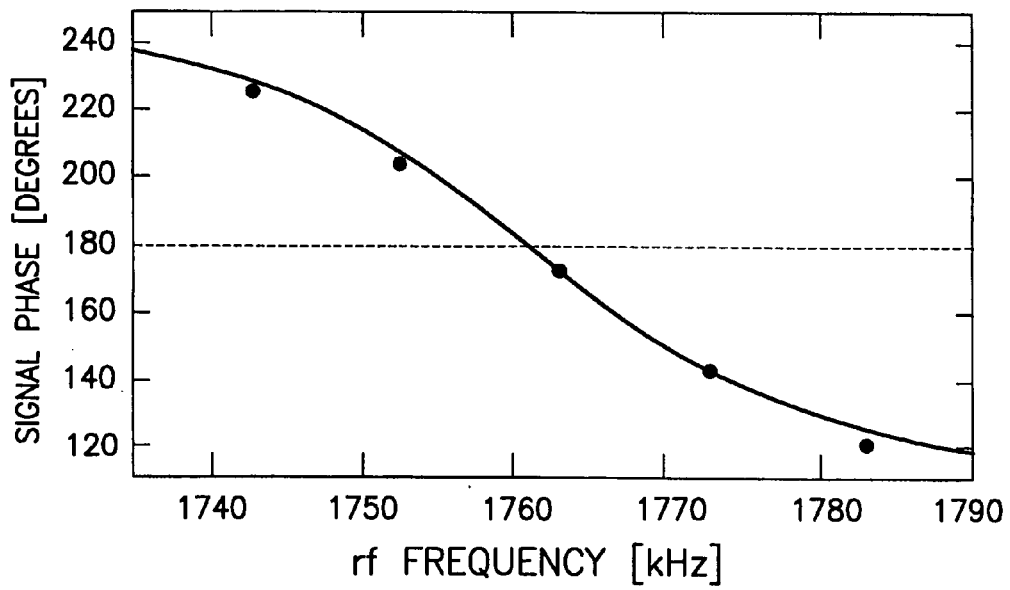
FIG. 10 is a graph of the signal phase versus rf frequency.

In FIG. 10, the circles represent measurements for no applied field, while the solid line represents $$\tan(\varphi) = -2Q_l\left(\frac{\omega_{rf}}{\omega_c} - \frac{\omega_c}{\omega_{rf}}\right)$$

using the independently measured value of $Q_l$ equal to 28. As depicted in this graph, the dependence of the phase on rf frequency shows excellent agreement with the theoretical prediction given above. This demonstrates that the measurement of the phase can be used to extract the antenna tuning through Equation (6). The nominal value of the phase on the resonance depends on the exact implementation of the phase cycling. In the above case, it is 180°.

The electronics of a specific NMR tool might exhibit additional phase shifts that should preferably be calibrated (including any potential temperature dependence). Such extra phase shifts will lead to an offset of the phase. However, with a proper calibration, the change in phase can still be used to infer the tuning of the antenna.

A standard electronic way to tune the antenna is the present TWST procedure: a signal of constant amplitude is injected into the calibration loop. The tuning of the antenna is changed to maximize the detected signal at the output of the spectrometer.

One modified electrical method to determine the resonance frequency of the antenna is to modulate a signal at the rf frequency $\omega_{rf}$ of the NMR pulses with a frequency $\omega_{mod}$. Best sensitivity is achieved if $\omega_{mod}$ is comparable to $$\frac{\omega_{rf}}{Q_l},$$

the width of the antenna resonance. The resulting signal, comprising of two frequencies $\omega_{rf} \pm \omega_{mod}$ of equal amplitude, is injected into the calibration loop and detected with the spectrometer. When the tool is on-resonance, the intensities of the two detected sidebands, $V_-$ and $V_+$ are equal. A potential detuning of the antenna, $\delta_\omega = \omega_c - \omega_{rf}$, can be inferred from the ratio of the detected intensities of the two sidebands, $V_-$ and $V_+$. To the first order, the detuning is given by:

$$\delta_\omega \cong \frac{1}{4}\left[\frac{\omega_{rf}^2}{4Q_l^2\omega_{mod}}\right]\left(1 - \frac{V_-}{V_+}\right) \quad (7)$$

Equation (7) can be used to estimate the change in tuning capacitance, and if necessary iteration can be used to find the final value.

Another method for measuring antenna tuning is based on time-multiplexed calibrations of tool responses at different frequencies. This measurement does not use the echo signal, it does not depend on the presence or strength of the echo signal and, therefore, it can drive a continuous feedback loop that keeps the antenna tuned. The amplitude calibration of the NMR measurement is performed periodically in-between measuring cycles, during the bursts-free "wait time" allowed for repolarization. It uses a fixed-amplitude test signal at the operating frequency that is a secondary standard derived from a laboratory calibration of the instrument. To measure antenna tuning, two additional calibration measurements are done but with the frequency of the test signal shifted by a small ±deviation around the operating frequency. This provides a three-point amplitude measurement of resonance and a quantitative value of the detuning from resonance.

With a second-order polynomial approximation of the resonance curve, if $y_1$, $y_2$, $y_3$ are the calibration amplitudes at the lower, center and upper frequencies and D is the frequency deviation, the antenna detuning in the vicinity of resonance is proportional to:

$$x = D*(y_1-y_3)/abs(2*y_2-y_1-y_3) \quad (8)$$

Figure 11:
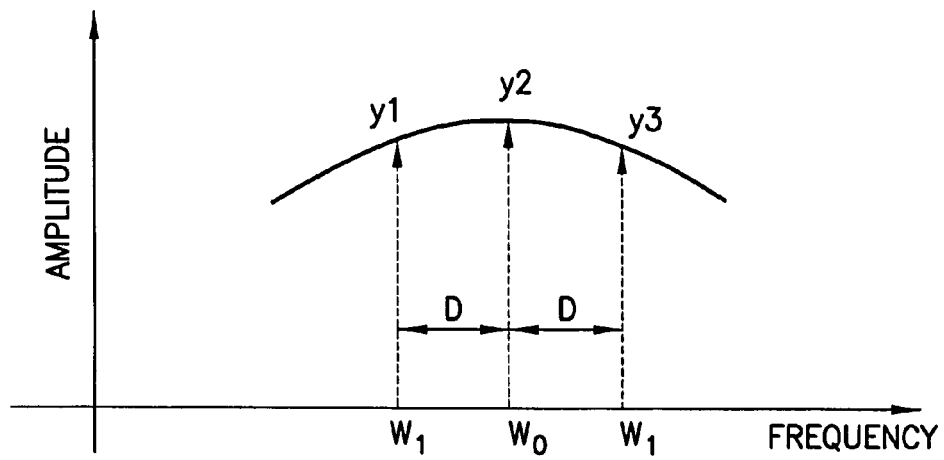
FIG. 11 is a graph showing an antenna resonance curve in accordance with the present invention.

The term $(2*y_2-y_1-y_3)$ reflects the curvature of the resonance curve as shown in FIG. 11 where $\omega_0$ is equal to the operating frequency, $\omega_1$ is equal to $\omega_0 \pm D$.

A positive curvature value (convex portion of the curve) gives a solid identification of the central zone of the resonance curve. The sign of the term $(y_1-y_3)$ reflects on what side of the resonance curve the antenna is operating.

With a detuning measurement performed for each CPMG, a feedback loop can adjust the antenna capacitance to maintain the antenna at resonance. By changing the capacitance of the antenna, a feedback loop based on this method can find the optimal point of antenna resonance over the whole range of capacitance/frequency values. The frequency deviation value D can be selected for optimum resolution versus signal-to-noise ratio of the measurement.

Figure 12:
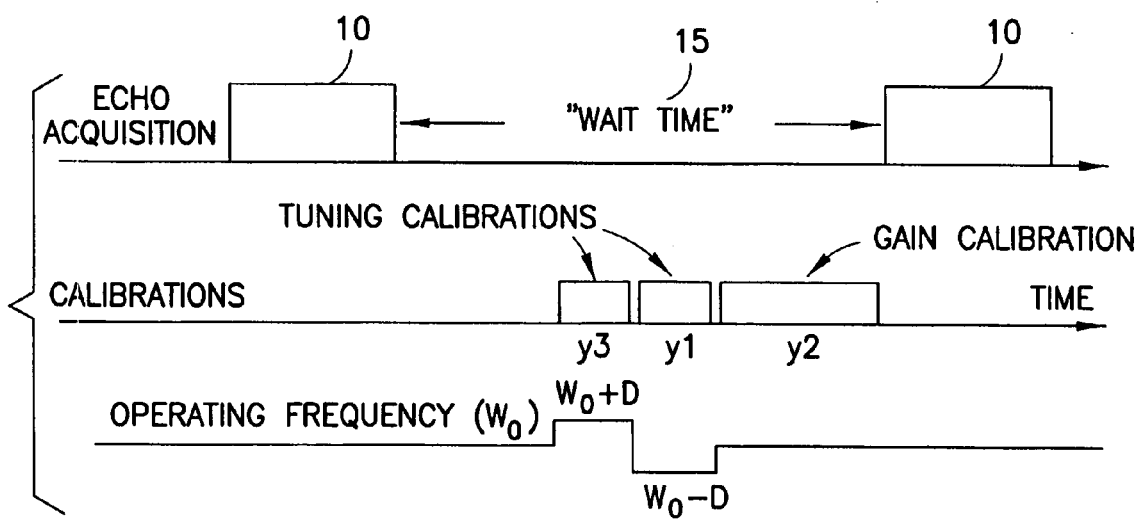
FIG. 12 is a schematic showing the antenna-tuning implementation of the present invention in Schlumberger's CMR™ tool.

The implementation of this measurement in Schlumberger's CMR™ tool follows the timing as shown in FIG. 12.

The three calibrations (y$_1$, Y$_2$, y$_3$) are performed at the end of the wait time, immediately before the next echo acquisition. For this tool, typical calibration times are 50 msec each at the upper and lower frequencies, followed by a 250 msec calibration at the center frequency. This last calibration is the traditional gain calibration. At the end of the echo acquisition that follows a set of antenna detuning measurements, the results are processed and a new value of tune-capacitor value (tune word) are computed and programmed in time for the next antenna detuning measurement.

Alternatively, antenna mistuning may be determined by analyzing the overall phases of the detected signals. As shown in FIG. 12, the phase of the signals 10 acquired after one or more wait times 15 may be compared to determine the antenna mistuning.

Figure 13:
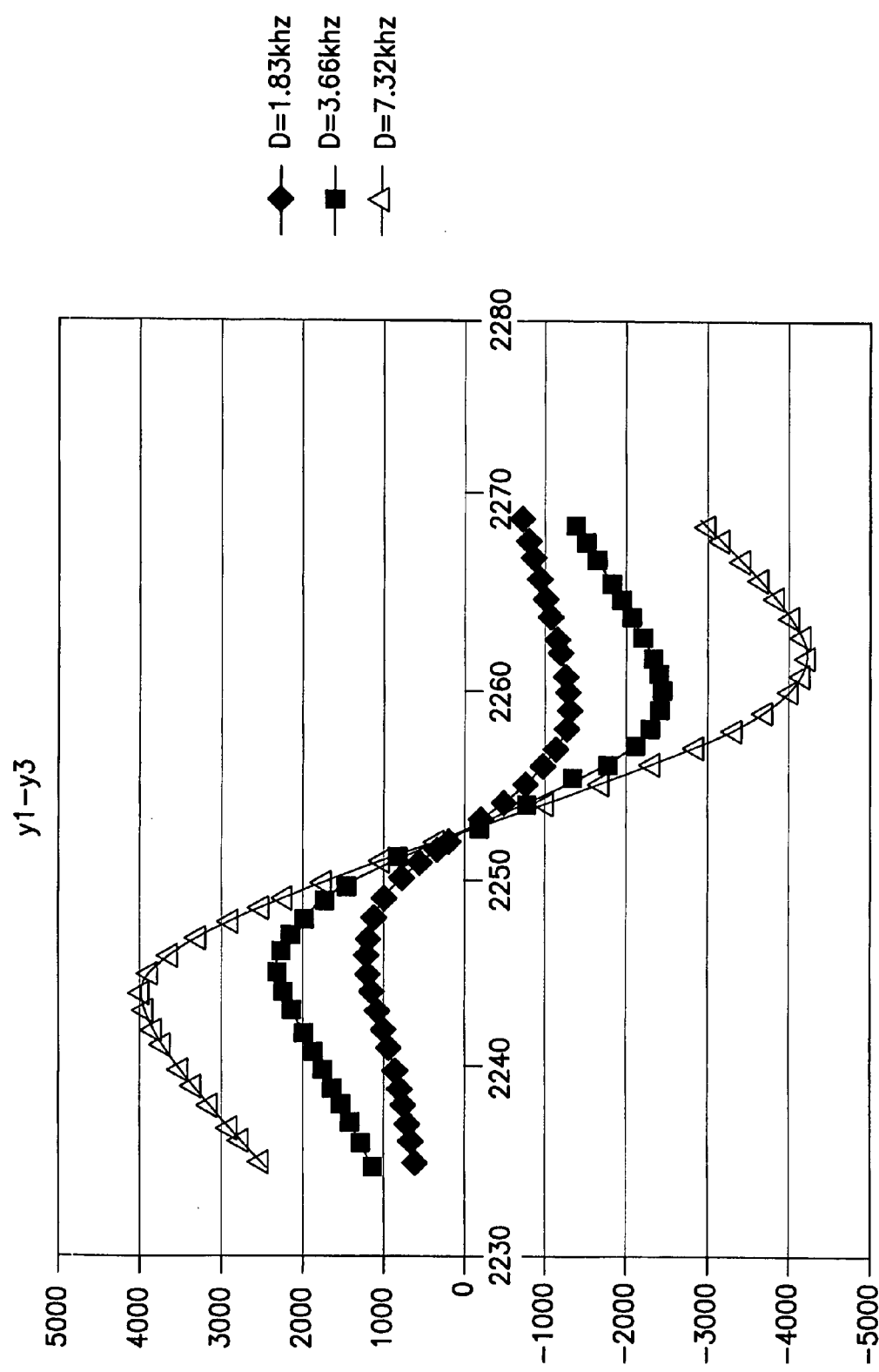
FIG. 13 is a graph showing measured differences between the calibration values taken at the frequencies deviated by −D and +D from the operating frequency as a function of the operating frequency.
Figure 14:
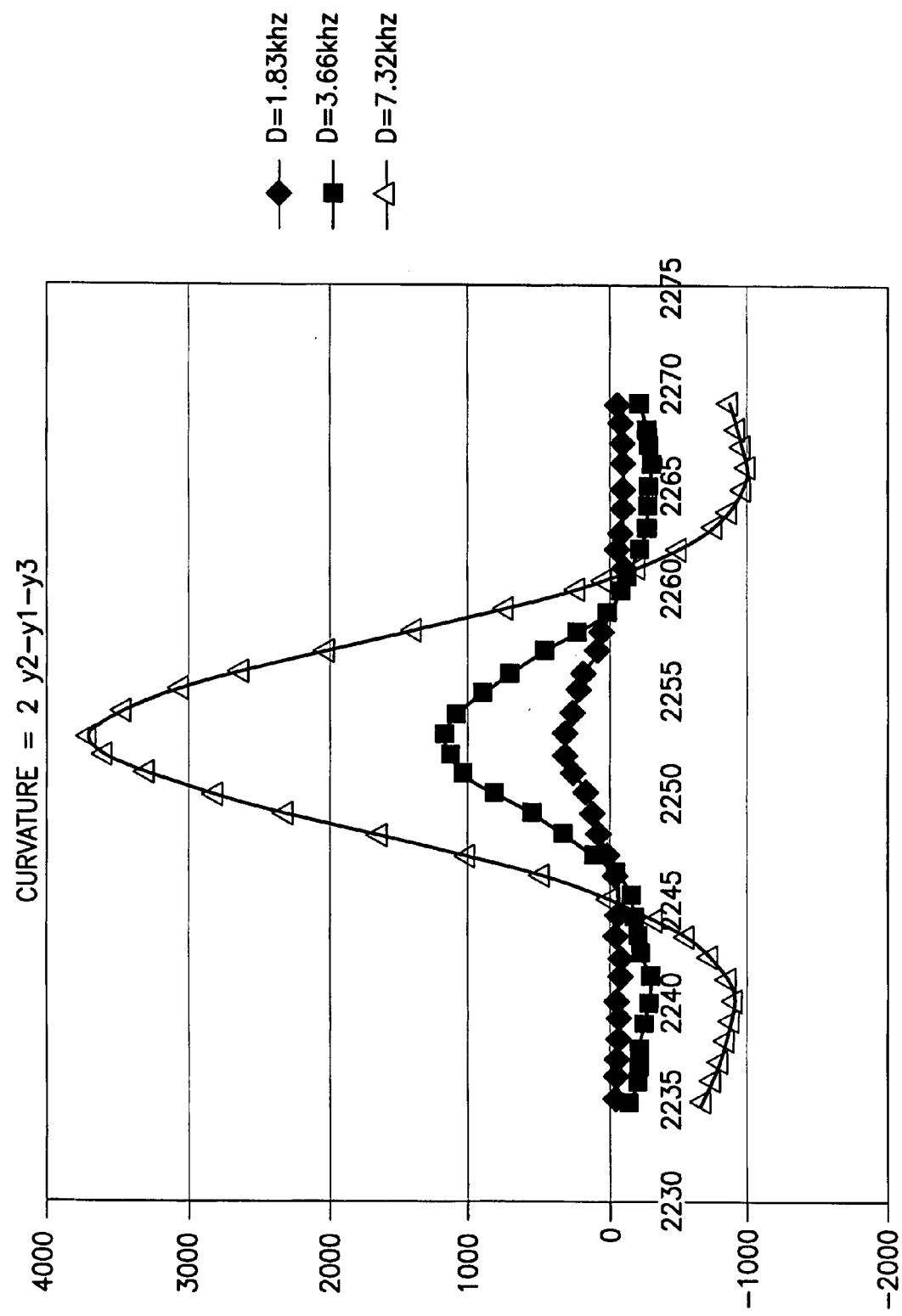
FIG. 14 is a graph of measured curvature values of the resonance curve that serve as indicators of proximity to the resonance frequency.
Figure 15:
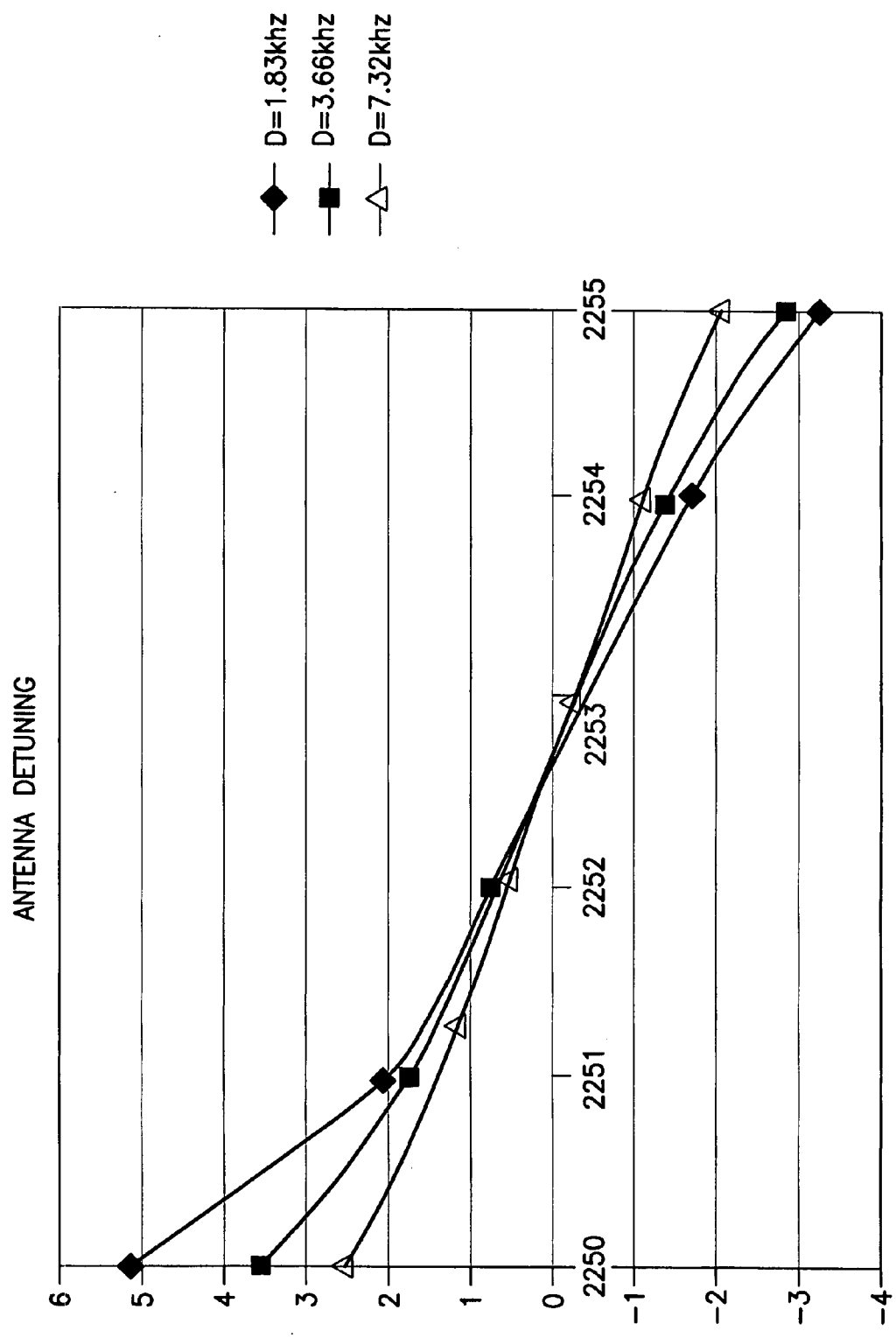
FIG. 15 is a graph showing measured antenna detuning factors.

Results of antenna detuning measurements made with three different frequency deviations D of 1.83, 3.66 and 7.32 kHz are shown in FIGS. 13, 14, and 15. The measurement points were taken with different operating frequencies and a fixed value of antenna capacitance that made the resonant frequency about 2250.5 kHz.

FIG. 13 shows measured differences (y$_1$-y$_3$) between the calibration values taken at the frequencies deviated by -D and +D from the operating frequency as a function of the operating frequency. The sign of this value depends on the side of the resonance curve the measurement is at, and, in the vicinity of resonance, the value is proportional to the detuning, although it depends here on the frequency step D.

FIG. 14 shows measured values of (2y$_2$-y$_1$-y$_3$) with a maximum at the resonance frequency. The interval where the value is positive can be used to define a condition of proximity to resonance.

FIG. 15 shows measured detuning factors x=D*(y$_1$-y$_3$)/abs(2*y$_2$-y$_1$-y$_3$) in the vicinity of resonance. This value is only slightly dependent on the frequency deviation D. This is the value a proportional feedback loop should use for optimum regulation.

The measuring of Larmor frequency deviation requires that there is sufficient signal amplitude to make measurements with adequate signal-to-noise ratio. This is not always the case during a continuous log in an oil well. A practical system should keep the current method of adjusting the operating frequency with tool temperature, while the feedback loop here described introduces an additional offset into the operating frequency. The feedback loop should respond depending on the quality of the signal present. The stronger the signal, the stronger/faster the loop response should be. In absence of signal, the loop should become dormant and the operating frequency should continue tracking with tool temperature and the last offset value from the loop until sufficient signal is present again for the loop to resume. Alternatively, the echoes may be stacked as described above.

It is noted that the expressions provided above are generally applicable to all NMR tools that have a maximum density of state. While some tools have density of states that are nearly vertically, one skilled in the art would recognize that perfectly vertical density of states are only achievable in highly controlled laboratory environments. In reality nearly all NMR tools have some variation of a saddle point (or maximum density of state), whether sharply defined (nearly vertical) or smooth. Accordingly, the equations and methodology presented herein may be applied (with minor modifications) to nearly all NMR tools, whether designed for medical, earth logging, or food characterization purposes.

Figure 16:
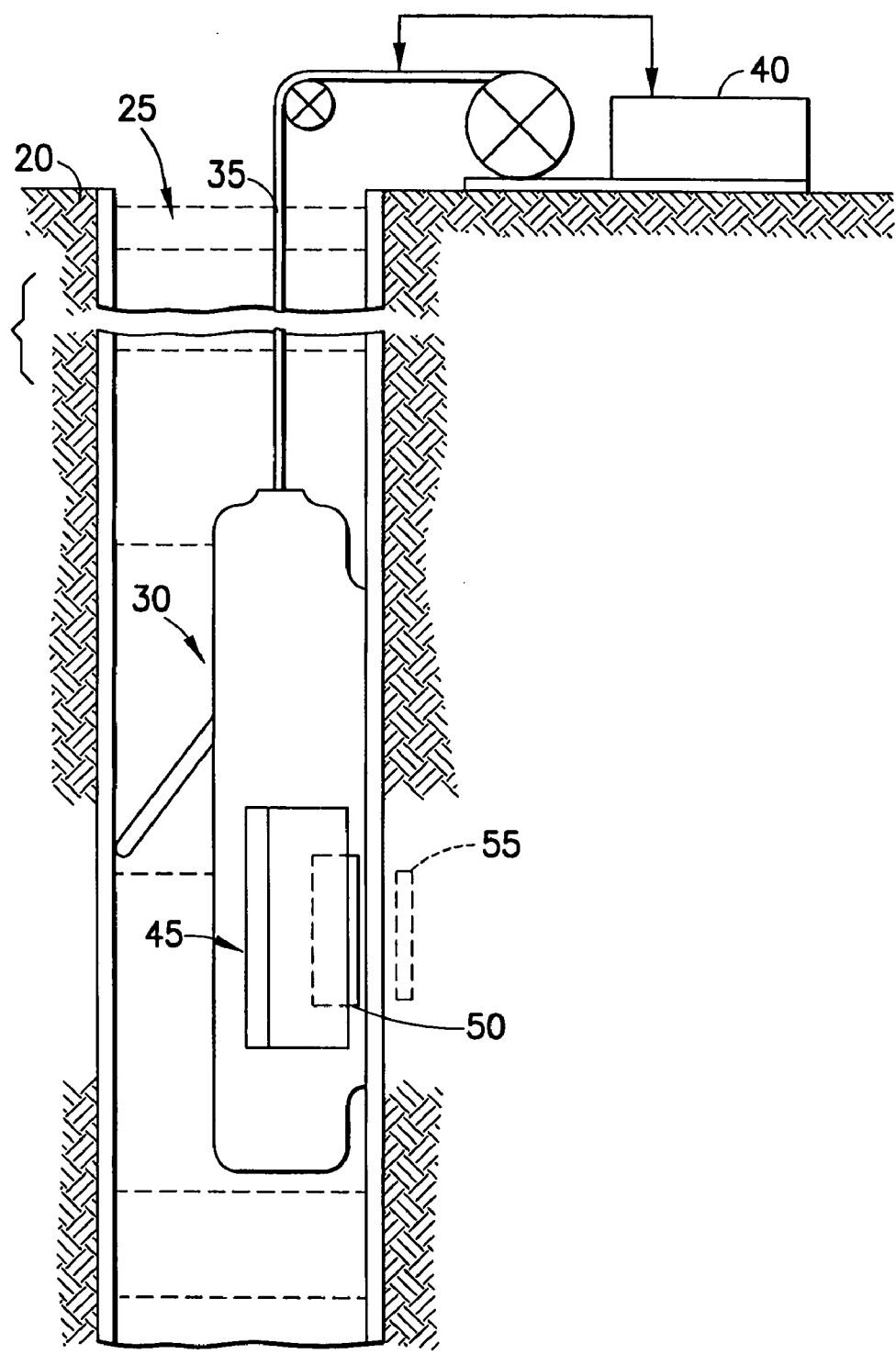
FIG. 16 is a schematic showing one implementation of the present invention.
Figure 17:
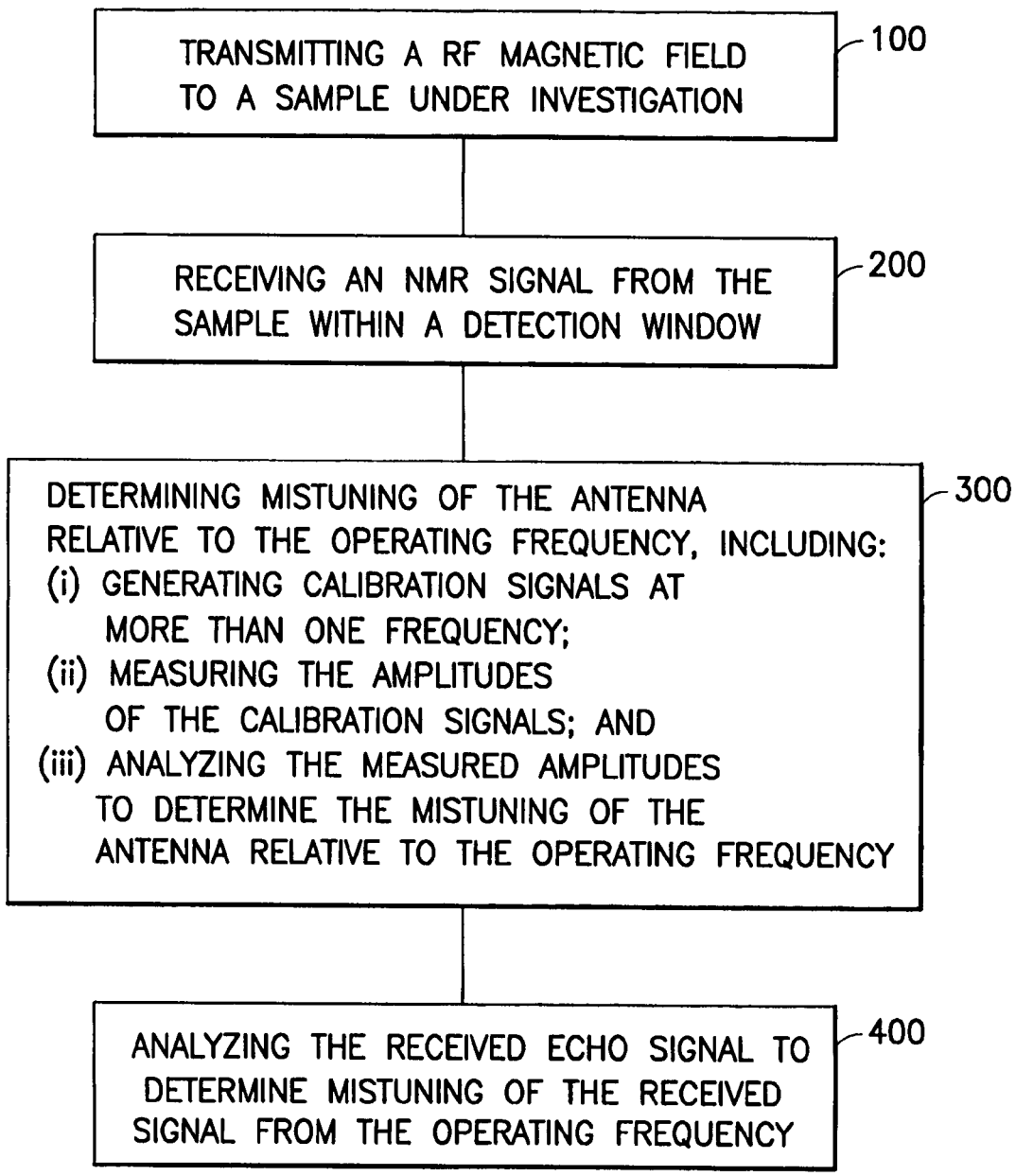
FIG. 17 is a flow chart reflecting one embodiment of the present invention.

FIG. 16 shows a non-limiting earth formation logging apparatus that can be utilized for practicing embodiments of the invention to investigate subsurface formations 20 traversed by a borehole 25. A magnetic resonance investigating apparatus or logging device 30 is suspended in the borehole 25 on an armored cable 35, the length of which substantially determines the relative depth of the device 30. The length of cable 35 is controlled by suitable means at the surface such as a drum and winch mechanism. Surface equipment, represented at 40, can be of conventional type, and can include a processor subsystem that communicates with all the downhole equipment. It will be understood that some of the processing can be performed downhole and that, in some cases, some of the processing may be performed at a remote location. Also, while a wireline embodiment is illustrated, alternative forms of physical support and communicating link can be used, for example in a measurement-while-drilling or logging-while-drilling system, fluid sample tool, in practicing the methods of the invention.

The logging device may include, for example, a permanent magnet or permanent magnet array 45, which may be made of a samarium-cobalt-magnetic material, and one or more rf antennas 50. The investigation region, or sensitivity zone, represented generally at 55, is a region in the formation in which the measurements are made. It will be understood that the present invention may be applicable to other tool configurations.

While the invention has been described herein with reference to certain examples and embodiments, it will be evident that various modifications and changes may be made to the embodiments described above without departing from the scope and spirit of the invention as set forth in the claims.

What is claimed is:

1. A method for tuning a nuclear magnetic resonance (NMR) tool, said tool having an operating frequency and equipped with an antenna, comprising:
   a. transmitting a rf magnetic field to a sample under investigation;
   b. receiving an NMR signal from said sample within a detection window;
   c. determining mistuning of said antenna relative to said operating frequency including:
      i. generating calibration signals at more than one frequency;
      ii. measuring the amplitudes of said calibration signals; and
      iii. analyzing said measured amplitudes to determine said mistuning of the antenna relative to said operating frequency; and
   d. analyzing the received echo signal to determine mistuning of the received signal from said operating frequency.

2. The method of claim 1 wherein analyzing said measured amplitudes includes identifying a maximum amplitude.

3. The method of claim 1, wherein determining mistuning of said antenna includes analyzing the signal phase of the received signal.

4. The method of claim 3, wherein analyzing the signal phase includes comparing the signal phase of said received signal to the signal phase of said transmitted signal to determine mistuning of said antenna.

5. The method of claim 4, further comprising inferring the tuning of the antenna based on the difference in phase between the received signal and the transmitted signal.

6. The method of claim 1, wherein analyzing the received echo signal includes analyzing the complex echo shape of the received echo signal.

7. The method of claim 1, further comprising:
   e. partitioning said detection window into more than one interval;
   f. detecting a plurality of signals in each interval wherein said plurality of signals includes in-phase and out-of-phase signals;
   g. analyzing at least two of said plurality of signals to determine mistuning of the received echo signal from said operating frequency.

8. The method of claim 7, wherein analyzing at least two of said plurality of signals includes analyzing in-phase signals and out-of-phase signals or any combination thereof.

9. The method of claim 8, wherein at least two of said plurality of signals are from the same interval.

10. The method of claim 8, wherein at least two of said plurality of signals are from different intervals.

11. The method of claim 7, further comprising:
    h. determining the slope of a signal detected in the out-of-phase channel at the signal center; and
    i. inferring the tuning of the operating frequency from said out-of-phase slope.

12. The method of claim 11, wherein said out-of-phase slope is approximated by determining the ratio of the out-of-phase portion of the detection window versus the in-phase portion of the detection window.

13. The method of claim 12, wherein said out-of-phase slope is approximated according to the ratio $\mathcal{R}$:

$$\mathcal{R} \equiv \frac{\left\{\int_{t_0}^{t_0+T/2} - \int_{t_0-T/2}^{t_0}\right\} dt S_{out\text{-}of\text{-}phase}(t)}{\int_{t_0-T/2}^{t_0+T/2} dt S_{in\text{-}phase}(t)}.$$

14. The method of claim 13, further comprising repeating a, b, h, and i one or more times and calculating an average $\mathcal{R}$.

15. The method of claim 1, wherein said calibration signal is modulated by a frequency approximately equivalent to the width of the antenna resonance.

16. The method of claim 15, further comprising measuring the intensity of sidebands corresponding to the modulated transmitted if magnetic field and the received calibration signal.

17. The method of claim 1, wherein said if magnetic field is a CPMG sequence.

18. The method of claim 1, further comprising calibrating and characterizing said NMR tool prior to tuning said NMR tool.

19. The method of claim 1, further comprising monitoring the temperature of magnets of said tool.

20. The method of claim 1, further comprising repeating (a), (b), (c), and (d) one or more times.

21. A method for tuning a nuclear magnetic resonance (NMR) tool, said tool having an operating frequency and equipped with an antenna, comprising:
    a. transmitting an if magnetic field to a sample under investigation;
    b. receiving an NMR echo from said sample within a detection window;
    c. determining mistuning of said antenna relative to said operating frequency, including
       i. generating calibration signals at more than one frequency;
       ii. measuring the amplitudes of said calibration signals; and
       iii. analyzing said measured amplitudes to determine said mistuning of the antenna relative to said operating frequency; and
    d. analyzing changes of phase along the received echo signal to determine mistuning of the received echo signal from the operating frequency.

22. The method of claim 21, wherein analyzing said measured amplitudes includes identifying a maximum amplitude.

23. The method of claim 21, wherein determining mistuning of said antenna includes analyzing the signal phase of the received signal.

24. The method of claim 21, wherein c and d are performed simultaneously.

25. The method of claim 24, wherein determining the mistuning of the antenna further includes obtaining time-multiplexed measurements of the antenna during an inactive portion of (a) and (b) wherein measurements are performed using a calibration signal.

26. The method of claim 25, wherein said calibration signal is modulated to at least two values deviated from the operating frequency.

27. The method of claim 21 further comprising repeating a, b, c, and d one or more times.

28. A method for tuning a nuclear magnetic resonance (NMR) logging tool, said tool having an operating frequency and equipped with an antenna, comprising:
    a. providing said NMR logging tool in a borehole traversing an earth formation;
    b. transmitting a if magnetic field to a region of investigation;
    c. receiving an NMR signal from said region of investigation within a detection window;
    d. determining mistuning of said antenna relative to said operating frequency including:
       (i) generating calibration signals at more than one frequency;
       (ii) measuring the amplitudes of said calibration signals; and
       (iii) analyzing said measured amplitudes to determine said mistuning of the antenna relative to said operating frequency; and
    e. analyzing the received echo signal to determine mistuning of the received signal from said operating frequency.

29. The method of claim 28, wherein said region of investigation is a section of earth formation.

30. The method of claim 28, wherein said region of investigation is an extracted sample of formation fluid.

31. The method of claim 28, wherein analyzing said measured amplitudes includes identifying a maximum amplitude.

32. The method of claim 28, wherein determining mistuning of said antenna includes analyzing the signal phase of the received signal.

33. The method of claim 32, wherein analyzing the signal phase includes comparing the signal phase of said received signal to the signal phase of said transmitted signal to determine mistuning of said antenna.

34. The method of claim 33, further comprising inferring the tuning of the antenna based on the difference in phase between the received signal and the transmitted signal.

35. The method of claim 28, wherein analyzing the received echo signal includes analyzing the complex echo shape of the received echo signal.

36. The method of claim 28, further comprising:
f. partitioning said detection window into more than one interval;
g. detecting a plurality of signals in each interval wherein said plurality of signals includes in-phase and out-of-phase signals;
h. analyzing at least two of said plurality of signals to determine mistuning of the received echo from said operating frequency.

37. The method of claim 36, wherein analyzing at least two of said plurality of signals includes analyzing in-phase signals and out-of-phase signals or any combination thereof.

38. The method of claim 37, wherein at least two of said plurality of signals are from the same interval.

39. The method of claim 37, wherein at least two of said plurality of signals are from different intervals.

40. The method of claim 36, further comprising:
i. determining the slope of a signal detected in the out-of-phase channel at the signal center; and
j. inferring the tuning of the operating frequency from said out-of-phase slope.

41. The method of claim 40, wherein said out-of-phase slope is approximated by determining the ratio of the out-of-phase portion of the detection window versus the in-phase portion of the detection window.

42. The method of claim 41, wherein said out-of-phase slope is approximated according to the ratio $\mathcal{R}$:

$$\mathcal{R} \equiv \frac{\left\{\int_{t_0}^{t_0+T/2} - \int_{t_0-T/2}^{t_0}\right\} dt\, S_{out\text{-}of\text{-}phase}(t)}{\int_{t_0-T/2}^{t_0+T/2} dt\, S_{in\text{-}phase}(t)}.$$

43. The method of claim 42, further comprising repeating b, c, i, and j one or more times and calculating an average $\mathcal{R}$.

The method of claim 31, wherein said calibration signal is modulated by a a frequency approximately equivalent to the width of the antenna resonance.

44. The method of claim 43, further comprising measuring the intensity of sidebands corresponding to the modulated transmitted if magnetic field and the received NMR signal.

45. The method of claim 28, further comprising monitoring the temperature of of magnets of said tool.

46. The method of claim 28, further comprising:
f. positioning said tool proximate a second region of investigation and
g. repeating b, c, d, and e.

47. The method of claim 46, further comprising repeating f and g one or more times.

48. A method for tuning a nuclear magnetic resonance (NMR) logging tool, said tool having an operating frequency and equipped with an antenna, comprising:
a. positioning said logging tool in a borehole traversing an earth formation;
b. transmitting an if magnetic field to a region under investigation;
c. receiving an echo signal from said region of investigation within a detection window;
d. determining mistuning of said antenna relative to said operating frequency including:
(i) generating calibration signals at more than one frequency;
(ii) measuring the amplitudes of said calibration signals; and
(iii) analyzing said measured amplitudes to determine said mistuning of the antenna relative to said operating frequency; and
e. analyzing changes of phase along the received echo signal to determine mistuning of the received NMR echo from the operating frequency.

49. The method of claim 48, wherein determining mistuning of said antenna includes measuring signal amplitudes at more than one frequency and identifying a maximum amplitude.

50. The method of claim 48, wherein determining mistuning of said antenna includes analyzing the signal phase of the received signal.

51. The method of claim 48, wherein c and d are performed simultaneously.

52. The method of claim 51, wherein determining the mistuning of the antenna further includes obtaining time-multiplexed measurements of the antenna during an inactive portion of (b) and (c) wherein measurements are performed using a calibration signal.

53. The method of claim 52, wherein said calibration signal is modulated to at least two values deviated from the operating frequency.

54. The method of claim 48, further comprising:
f. positioning said tool proximate a second region of investigation and
g. repeating b, c, d, and e.

55. The method of claim 54, further comprising repeating f and g one or more times.

* * * * *